United States Patent

Derosa et al.

[11] Patent Number: 5,491,256
[45] Date of Patent: Feb. 13, 1996

[54] COMPOSITION OF MATTER FOR ALIPHATIC-AROMATIC UREAS, BIURETS, AND ALLOPHANATES AS NITRIC OXIDE REDUCING AGENTS IN DIESEL EMISSIONS

[75] Inventors: Thomas F. Derosa, Passaic, N.J.; Rodney L. Sung, Fishkill; Benjamin J. Kaufman, Hopewell Jct., both of N.Y.

[73] Assignee: Texaco Inc., White Plains, N.Y.

[21] Appl. No.: 222,509

[22] Filed: Apr. 4, 1994

Related U.S. Application Data

[63] Continuation of Ser. No. 976,634, Nov. 16, 1992, abandoned.

[51] Int. Cl.$^6$ .................................................. C07C 269/00
[52] U.S. Cl. .................................................. 560/132
[58] Field of Search ........................................ 560/132, 159

[56] References Cited

U.S. PATENT DOCUMENTS 4,336,402   6/1982   Falcone et al. .................... 560/148
4,692,550   9/1987   Engbert et al. .................... 560/345

OTHER PUBLICATIONS

Beilstein 1785462; RN=85997-51-9, 1937.
Casold 53:7046h; RN=109310-58-9, 1959.
Chemical Abstracts 108:123833e 1987.
Chemical Abstracts 84:75514D 1975.
Chemical Abstracts 55:15383 i,g,h; 1961.

*Primary Examiner*—José G. Dees
*Assistant Examiner*—Samuel Barts
*Attorney, Agent, or Firm*—George J. Darsa

[57] ABSTRACT

A composition of matter comprising ureas, biurets or allophanates structurally represented, respectively, by

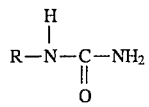

where R is hydrogen or a ($C_1$-$C_{50}$) linear or branched aliphatic, alkenyl, alkynyl or aryl hydrocarbon;

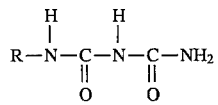

where R is hydrogen or a ($C_1$-$C_{50}$) linear or branched aliphatic, alkenyl, alkynyl or aryl hydrocarbon; or

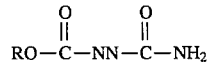

where R is hydrogen or a ($C_1$-$C_{50}$) linear or branched aliphatic, alkenyl, alkynyl or aryl hydrocarbon.

1 Claim, No Drawings

COMPOSITION OF MATTER FOR ALIPHATIC-AROMATIC UREAS, BIURETS, AND ALLOPHANATES AS NITRIC OXIDE REDUCING AGENTS IN DIESEL EMISSIONS

This is a continuation of application Ser. No. 07/976,634, filed on Nov. 16, 1992, now abandoned.

BACKGROUND OF THE INVENTION

This composition of matter relates to a chemical method of decreasing nitric oxide, NOx, levels. The chemical method utilizes chemical materials and methods that are well known in the art. The chemicals utilized by this composition of matter patent are reducing agents. When these reducing agents come in contact with NOx, the latter is reduced to non-toxic or environmentally friendly substances.

Nitrogen oxides are the oxidation products of elemental nitrogen, organic, or inorganic nitrogen and oxygen at elevated temperatures. Nitrogen oxides include nitric oxide, NO; nitrogen dioxide, $NO_2$; nitrogen trioxide, $NO_3$; dinitrogen trioxide, $N_2O_3$; tetranitrogen pentaoxide, $N_2O_5$; tetranitrogen hexaoxide, $N_4O_6$; nitrous oxide, $N_2O$; and the like. Elevated temperatures required to prepare these oxidation products are routinely obtained in internal combustion engines utilizing gasoline, diesel, or aviation fuel.

There are cogent ecological and environmental reasons to reduce or ideally eliminate NOx as an internal combustion oxidation product. Once produced, NOx is directly responsible for acid rain and photochemical smog. Moreover, chronic exposure to NOx has been directly linked with restricted pulmonary compliance in non-smoking healthy males; acute respiratory disease among children living in "high exposure" towns in Czechoslovakia; and a key irritant cited for the high incidence of chronic bronchitis among Japanese postal workers servicing urban centers as outlined in Medical and Biologic Effects of Environmental Pollutants by the National Academy of Sciences, 1977.

DISCLOSURE STATEMENT

Numerous chemical and physical methods have been suggested to reduce or eliminate NOx. Certain proposed techniques involve a great deal of capital outlay and require major consumption of additives, scrubbers, etc. For example, U.S. Pat. No. 3,894,141 proposes a reaction with liquid hydrocarbons; U.S. Pat. No. 4,405,587 proposes high temperature burning with a hydrocarbon; U.S. Pat. No. 4,448,899 proposes reacting with an iron chelate; U.S. Pat. No. 3,262,751 reacts NOx with a conjugated diolefin. Other methods utilize reactions with nitriles (U.S. Pat. No. 4,080,425), organic N-compounds amines or amides (U.S. Pat. No. Des. 3,324,668) or pyridine (J57190638). Application of these reactions imposes organic pollutant disposal problems along with the attendant problems of toxicity and malodorous environments. In addition, they require the presence of oxygen and are relatively expensive. Other systems are based on urea reactions. For example U.S. Pat. No. 4,119,702 uses a combination of urea and an oxidizing agent which decomposes it e.g., ozone, nitric acid, inter alia; U.S. Pat. No. 4,325,924 utilizes urea in a high temperature reducing atmosphere; and U.S. Pat. No. 3,900,554 (the thermodenox system) utilizes a combination of ammonia and oxygen to react with nitric oxide. All of these methods must deal with the problem of the odor of ammonia and its disposal. All require oxygen and other oxidizing agents. These methods also suffer from the drawback of requiring controlled environments which make them difficult to use in mobile vehicles or smaller stationary devices.

Back et al, Can J.Chem. 46,531 (1968), discusses the effect of NOx on the photolysis of isocyanic acid, HNCO, the decomposition product of cyanuric acid. Increased nitrogen levels in the presence of nitric oxide were observed utilizing a medium pressure mercury lamp for HNCO photolysis. Despite several remaining uncertainties, it was clear that nitric oxide levels were reduced when contact with isocyanic acid or its dissociation products was effected. A readily available source of isocyanic acid is via the thermal decomposition or unzipping of the corresponding trimer, cyanuric acid, $(HNCO)_3$.

Others disclosures especially as noted by Epperly et al in U.S. Pat. Nos. 4,770,863 and 5,017,347 and Bowers in 4,927,612 report the use of allophanates as another source of isocyanic acid. It may be inferred that these methods also have limited applicability in non-stationary power generators because of their very limited solubility in non-polar solvents, most notably, diesel fuel.

Thus, an object of the present invention is to provide chemical preparation of isocyanic acid from a material that is a diesel fuel-soluble precursor for non-stationary power generators.

SUMMARY OF THE INVENTION

The present invention provides a composition of matter comprising substituted ureas, biurets, or alophanates structurally represented, respectively, by:

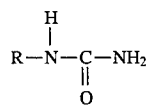

where R is hydrogen or a ($C_1$–$C_{50}$) linear or branched aliphatic, alkenyl, alkynyl or aryl hydrocarbon;

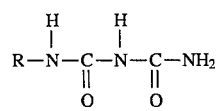

where R is hydrogen or a ($C_1$–$C_{50}$) linear or branched aliphatic, alkenyl, alkynyl or aryl hydrocarbon; or

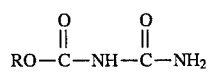

where R is hydrogen or a ($C_1$–$C_{50}$) linear or branched aliphatic, alkenyl, alkynyl or aryl hydrocarbon, respectively, which are soluble in diesel fuel and, upon thermal decomposition, generate isocyanic acid.

DETAILED DISCUSSION OF THE INVENTION

The present invention provides a composition of matter comprising substituted ureas (I), biurets (II) or allophanates (III) structurally represented as follows:

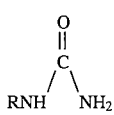

Urea

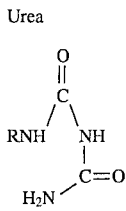

Biuret

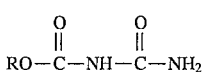

Allophanate where R is hydrogen or a ($C_1$–$C_{50}$) linear or branched aliphatic, alkenyl, alkynyl or aryl hydrocarbon. Moreover, it may contain one or more heteroatoms especially, but not restricted to, elements comprising Groups Va, VIa, and VIIa, or mixtures of these heteroatoms.

In the above structures, the allophanate R may be para-nonylphenyl, a ($C_{12}H_{25}$) aliphatic hydrocarbon or a ($C_8$–$H_{17}$) aliphatic hydrocarbon; the biuret R may be a ($C_6C_{13}$) aliphatic hydrocarbon, a ($C_{12}$–$H_{25}$) aliphatic hydrocarbon or para-nonylphenyl; and the urea R may be n-hexyl or para-methyl phenyl.

In addition, the present composition of matter invention provides a method of solubilizing ureas, biurets, and allophanates in diesel fuel that upon their thermal decomposition generate isocyanic acid (IV), as shown below, an effective nitric oxide reducing agent.

Isocyanic Acid (IV)

This composition of matter application is targeted as a diesel fuel additive. The method entails solubilizing ureas, biurets, and allophanates in diesel fuel so that upon thermal decomposition during the combustion event, the nitric oxide reducing agent, isocyanic acid, is generated. Empirically we have discovered that optimum diesel fuel solubility is achieved using aliphatic-aromatic ureas, biurets, or allophanates The chemical underpinning of this invention is generating isocyanic acid, HNCO, to reduce nitrogen oxide (NOx) emissions to environmentally friendly materials as depicted below in Equation (Eq.) 1. Isocyanic acid is generated quantatively by thermally decomposing cyanuric acid as shown below in Equation (Eq.) 2; however cyanuric acid technology

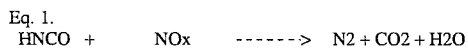

has very limited applicability to non-stationary NOx power plants because of its insolubility in diesel fuel. Moreover, derivatizing cyanuric acid to enhance its diesel fuel solubility proportionately diminishes its latent isocyanic acid capacity as shown below in Equations (Eqs.) 3, 4, and 5.

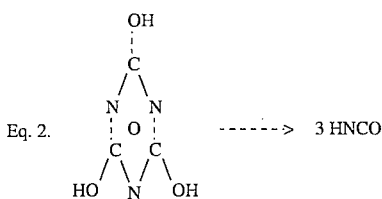

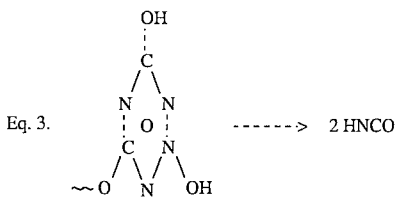

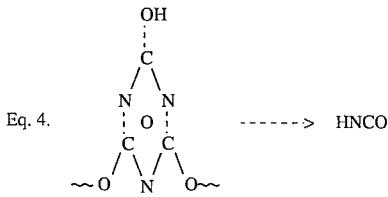

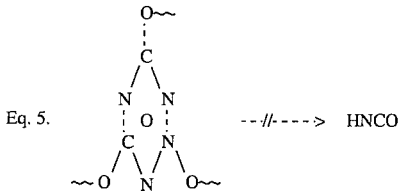

Thus, the thrust of the present invention is both the use of ureas (I), biurets (II), and allophanates (III) as thermal sources of isocyanic acid as shown below in Equations (Eqs.) 6, 7, and 8, respectively, and their aliphatic-aromatic derivativation to ensure high diesel fuel solubility.

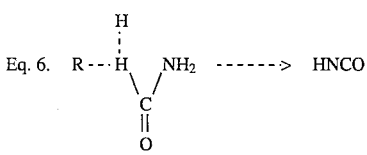

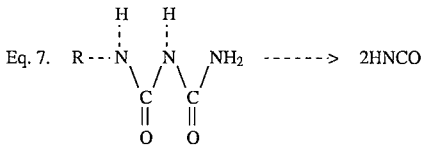

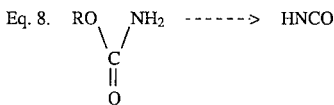

Heretofore, the essential aliphatic-aromatic structural requirements to ensure high diesel fuel solubility of corresponding ureas, biurets, and allophanates has been generically represented by R. Structurally, R is represented by the following:

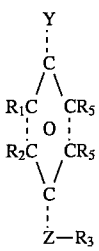

where $R_1, R_2, R_3, R_4$, and $R_5$ are each hydrogen or a $(C_1-C_{50})$ linear or branched, aliphatic, alkenyl, alkynyl or aryl hydrocarbon; and Y and Z may be a $(C_1-C_5)$ linear aliphatic, alkenyl or alkynyl hydrocarbon or a group consisting of Group Va, Group VIa, and Group VIIa materials of the periodic table.

In order to further illustrate the present invention and its advantages, the following Examples are provided. It is understood, however, that these Examples do not limit the scope nor application of this invention as defined in the appended claims.

EXAMPLE 1

Preparation of p-nonylphenylallophanate

A 500 ml 3-neck round bottom flask containing a magnetic stirrer, thermometer, and a gas egress tube is charged with 1 part p-nonylphenol and three parts urea. The flask is immersed in oil at 145° C. or any other elevated temperature to ensure that urea is thoroughly melted and efficient stirring occurs for two hours. The reaction mixture is then cooled and p-nonylphenyl-allophanate solvent extracted using n-heptane. Infrared absorbance at 3270 cm—1 (N—H stretching) and at 1705 cm–1 (C=O stretching) in addition to the conspicuous absence of any absorbance at 3450 cm–1 (O—H stretching) confirm the chemical transformation.

EXAMPLE 2

Preparation of dodecylallophanate

In this Example, docecyl alcohol was substituted for the p-nonylphenol in the aforementioned Example 1 to obtain the product of the present Example.

EXAMPLE 3

Preparation of octylallophanate

In this example octyl alcohol was substituted for the p-nonylphenol in the aforementioned Example 1 to obtain the product of the present Example.

EXAMPLE 4

Preparation of n-hexylbiuret

In this Example, n-hexylamine was substituted for the p-nonylphenol in the aforementioned Example 1 to obtain the product of this Example. In this Example, infrared absorbance at 3265 cm–1 (N—H stretching) and 1680 cm–1 (C=O stretching) in addition to the conspicuous absence of any absorbance at 3350 cm–1 (N—H stretching) was supportive of a chemical transformation.

EXAMPLE 5

Preparation of p-dodecoxyphenylbiuret

In this Example, p-dodecoxyaniline was substituted for the p-nonylphenol in the aforementioned Example 1 to obtain the product of the present Example.

EXAMPLE 6

Preparation of p-nonoxyphenylbiuret

In this Example, p-nonoxyaniline was substituted for the p-nonylphenol in the aforementioned Example 1 to obtain the product of the present Example.

EXAMPLE 7

Preparation of n-hexyl triuret

In this Example, the general procedure as outlined in Example 1 was again utilized with these modifications. The initial reactor was charged with three parts urea and one part amine. The reaction was heated for two hours whereupon a fourth part of urea is quickly added and the mixture heated for an addition hour. The triuret was solvent extracted using n-heptane. Infrared absorbance at 3300 cm–1 and 3284 cm–1 (interior and terminal N—H stretching, respectively), 1670 cm–1 (C=O) in addition to the conspicuous absence of any absorbance at 3400 to 3350 cm–1 (amine N—H stretching) was evidence of a chemical transformation.

EXAMPLE 8

Preparation of p-dodecoxyphenyltriuret

In this Example, p-Dodecoxyaniline was substituted for the p-nonylphenol in the aforementioned Example 1 to obtain the product of the present Example.

EXAMPLE 9

Preparation of p-nonoxyphenyltriuret

In this Example, p-Nonoxyaniline was substituted for the p-nonylphenol in the aforementioned Example 1 to obtain the product of the present Example.

The materials synthesized according to the present invention were structurally and physically evaluated. The structural property of interest was the was the detection of allophanates, biurets, or triurets and was determined using photospectrometric methods. It was fingerprinted by examining infrared absorbance between 3300 cm–1 and 3200 cm–1 (N—H stretch) and 1710 cm–1 to 1640 cm–1 (C=O stretch). Results of diesel fuel solubility and thermal stability of the neat experimental samples are summarized below in Table I.

EXAMPLE 10

Preparation of n-hexylurea

In this Example the procedure in Example 1 was utilized but using one part n-hexylamine and 1.5 part urea to obtain the product of the present Example.

EXAMPLE 11

Preparation of (p-methyl)phenylurea

In this Example p-methylaniline was substituted for n-hexylamine in the aforementioned Example 10 to obtain the product of the present Example.

TABLE I

Summary of diesel fuel solubility and thermal properties of substituted allophanates, biurets, and triurets.

| Material | Diesel Fuel Solubility at Turbidity Point* (wt %) | 50 wt % Decomposition Temperature (deg C.) | 90 wt. % Decomposition Temperature (deg C.) |
|---|---|---|---|
| Unmodified urea | 0.1 | 175 | 195 |
| Unmodified biuret | 0.1 | 210 | 245 |
| Unmodified triuret | 0.1 | 310 | 355 |
| Example 1 | <30% | 450 | 510 |
| Example 2 | <30% | 420 | 485 |
| Example 3 | <25% | 420 | 490 |
| Example 4 | <30% | 430 | 510 |
| Example 5 | <30% | 420 | 505 |
| Example 6 | <30% | 430 | 480 |
| Example 7 | ~15% | 440 | 610 |
| Example 8 | ~15% | 440 | 675 |
| Example 9 | ~15% | 440 | 615 |
| Example 10 | ~25% | 340 | 510 |
| Example 11 | ~12% | 385 | 575 |

*TGA's were conducted with a heating rate of 200 deg under air.

From the results of Table I above, it is clear that enhanced diesel fuel solubility and thermal stability of this additive result when this unique experimental approach is utilized.

We claim:

1. A composition of matter comprising a substituted allophonate structurally represented by the formula:

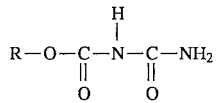

where R is para-nonylphenyl.

* * * * *